United States Patent
Suda et al.

(10) Patent No.: US 8,424,822 B2
(45) Date of Patent: Apr. 23, 2013

(54) ULTRASOUND DIAGNOSIS APPARATUS

(75) Inventors: Masahiko Suda, Mitaka (JP); Takayoshi Saito, Mitaka (JP)

(73) Assignee: Hitachi Aloka Medical, Ltd., Mitaka-shi, Tokyo (JP)

( * ) Notice: Subject to any disclaimer, the term of this patent is extended or adjusted under 35 U.S.C. 154(b) by 1059 days.

(21) Appl. No.: 11/826,253

(22) Filed: Jul. 13, 2007

(65) Prior Publication Data

US 2008/0048091 A1 Feb. 28, 2008

(30) Foreign Application Priority Data

Jul. 18, 2006 (JP) .................... 2006-195105

(51) Int. Cl.
*E04G 3/00* (2006.01)

(52) U.S. Cl.
USPC .................. 248/282.1; 248/274.1; 248/276.1; 248/415; 248/131; 248/919; 361/679.06; 361/679.04; 345/905

(58) Field of Classification Search .............. 248/274.1, 248/276.1, 282.1, 283.1, 289.11, 415, 131, 248/919, 920; 361/679.01, 679.06, 679.21; 600/300; 345/659

See application file for complete search history.

(56) References Cited

U.S. PATENT DOCUMENTS

| | | | | |
|---|---|---|---|---|
| 471,732 A * | 3/1892 | Goehst | ................... | 248/282.1 |
| 999,283 A * | 8/1911 | White | ................... | 248/282.1 |
| 4,319,314 A * | 3/1982 | Morton | ................... | 362/432 |
| 4,708,312 A * | 11/1987 | Rohr | ................... | 248/281.11 |
| 5,177,616 A * | 1/1993 | Riday | ................... | 348/837 |
| 5,490,652 A * | 2/1996 | Martin | ................... | 248/282.1 |
| 5,618,090 A * | 4/1997 | Montague et al. | ................... | 312/209 |
| 5,829,307 A | 11/1998 | Harima et al. | | |
| 5,924,988 A * | 7/1999 | Burris et al. | ................... | 600/437 |
| 5,941,824 A * | 8/1999 | Hwang | ................... | 600/437 |
| 6,095,468 A * | 8/2000 | Chirico et al. | ................... | 248/282.1 |

(Continued)

FOREIGN PATENT DOCUMENTS

DE 4316590 11/1993
DE 29702047 U 6/1997

(Continued)

OTHER PUBLICATIONS

European Search Report dated Dec. 27, 2007, Application No. 07013317.8-1265.

(Continued)

*Primary Examiner* — Terrell McKinnon
*Assistant Examiner* — Michael McDuffie
(74) *Attorney, Agent, or Firm* — Westerman, Hattori, Daniels & Adrian, LLP

(57) ABSTRACT

An ultrasound diagnosis apparatus having a display supported by an arm mechanism is provided. The arm mechanism has a first arm member and a second arm member. A turning mechanism is provided at a base end portion of the first arm member and a turning mechanism is provided at a working end portion of the second arm member. An upper end portion of the first arm member and a lower end portion of the second arm member form a connection section, and an intermediate turning mechanism is provided inside the connection section. Because the arm mechanism is gently curved over its entire structure, no excessive load is applied to the cable passing inside the arm mechanism. The cable extends in the connection section along an outer route having a gentle radius of curvature.

7 Claims, 6 Drawing Sheets

U.S. PATENT DOCUMENTS

| | | | |
|---|---|---|---|
| 6,409,134 B1 * | 6/2002 | Oddsen, Jr. | 248/274.1 |
| 6,601,811 B1 * | 8/2003 | Van Lieshout | 248/282.1 |
| 6,669,639 B1 * | 12/2003 | Miller et al. | 600/443 |
| 6,695,270 B1 * | 2/2004 | Smed | 248/274.1 |
| 6,758,454 B2 * | 7/2004 | Smed | 248/314 |
| 6,817,585 B2 * | 11/2004 | Wagner et al. | 248/324 |
| 6,935,883 B2 * | 8/2005 | Oddsen, Jr. | 439/374 |
| 7,004,437 B2 * | 2/2006 | Bauer et al. | 248/282.1 |
| 7,042,714 B2 * | 5/2006 | Hillman et al. | 361/679.21 |
| 7,066,435 B2 * | 6/2006 | Oddsen et al. | 248/220.43 |
| 7,216,382 B2 * | 5/2007 | Newkirk et al. | 5/600 |
| 7,246,780 B2 * | 7/2007 | Oddsen, Jr. | 248/282.1 |
| 7,461,825 B2 * | 12/2008 | Olivera et al. | 248/282.1 |
| 2001/0023914 A1 | 9/2001 | Oddsen, Jr. | |
| 2002/0066843 A1 | 6/2002 | Oddsen, Jr. et al. | |
| 2003/0086240 A1 | 5/2003 | Jobs et al. | |
| 2003/0141426 A1 | 7/2003 | Wagner et al. | |
| 2004/0178312 A1 * | 9/2004 | Parsons | 248/276.1 |
| 2004/0183410 A1 | 9/2004 | Dubon | |
| 2004/0218352 A1 | 11/2004 | Hillman et al. | |
| 2004/0228080 A1 | 11/2004 | Hillman et al. | |
| 2004/0233623 A1 | 11/2004 | Hillman et al. | |
| 2004/0251390 A1 | 12/2004 | Wachob | |
| 2004/0257755 A1 | 12/2004 | Hillman et al. | |
| 2004/0262484 A1 | 12/2004 | Wagner et al. | |
| 2005/0036283 A1 | 2/2005 | Hillman et al. | |
| 2005/0041048 A1 | 2/2005 | Hillman et al. | |
| 2005/0088812 A1 | 4/2005 | Hillman et al. | |
| 2005/0088814 A1 | 4/2005 | Jobs et al. | |
| 2006/0091769 A1 | 5/2006 | Dubon | |
| 2006/0176655 A1 | 8/2006 | Hillman et al. | |
| 2006/0284037 A1 * | 12/2006 | Dittmer et al. | 248/285.1 |
| 2006/0284531 A1 | 12/2006 | Dubon | |
| 2007/0014084 A1 | 1/2007 | Jobs et al. | |
| 2007/0095992 A1 * | 5/2007 | Dozier | 248/276.1 |
| 2007/0201197 A1 | 8/2007 | Hillman et al. | |

FOREIGN PATENT DOCUMENTS

| | | |
|---|---|---|
| JP | 6-296254 A | 10/1994 |
| JP | 10/216126 A | 8/1998 |
| JP | 2002/300496 A | 10/2002 |
| JP | 2004/344636 A | 12/2004 |
| JP | 2005-508681 A | 4/2005 |
| JP | 2005-264972 A | 9/2005 |
| JP | 2005-531791 A | 10/2005 |
| JP | 2007/097775 A | 4/2007 |
| JP | 2007/520305 A | 7/2007 |
| WO | WO 2005/074806 A1 | 8/2005 |
| WO | WO 2005/074806 A1 | 8/2005 |
| WO | WO 2005/074807 A1 | 8/2005 |

OTHER PUBLICATIONS

Japanese Notice of Grounds for Rejection dated Aug. 19, 2008 corresponding with Japanese Application No. 2006-195105.

Notice of Grounds for Rejection dated May 10, 2011, issued in corresponding Japanese Patent Application No. 2009-008746.

* cited by examiner

ULTRASOUND DIAGNOSIS APPARATUS

BACKGROUND OF THE INVENTION

1. Field of the Invention

The present invention relates to an ultrasound diagnosis apparatus, and in particular to an improvement in an arm mechanism which supports a display unit.

2. Description of the Related Art

An ultrasound diagnosis apparatus is a device which forms an ultrasound image based on a reception signal obtained by transmission and reception of an ultrasound and displays the formed image. The ultrasound image is displayed on a display mounted on the body of the apparatus. Although CRT (cathode ray tube) display have been commonly used in the related art, it is expected that use of flat panel displays such as liquid crystal displays and plasma displays will increase. Arm mechanisms are commonly used to support the display with the body of the apparatus (such as a housing, a support column, an operation panel, etc.), and such arm mechanisms generally have a plurality of joint sections so that the position and orientation of the display can be varied.

U.S. Pat. No. 6,669,639 relates to an ultrasound diagnosis apparatus and discloses an arm mechanism on which a CRT is mounted as a display. The arm mechanism comprises a first arm and a second arm. Each arm has a shape of a flat plate and extends in a slanted direction. At a connection section between the first arm and the second arm, a rotation mechanism is provided. At the connection section, an axis of the first arm and the axis of the second arm intersect each other at an acute angle. If a cable for the display is routed inside the connection section, the cable may be damaged due by repeated operation of the rotation mechanism over time, while if the cable is provided outside of the arm mechanism, the cable may block movement of the display or operation on the operation panel and the appearance would be degraded. International Patent Publication No. WO2005/074806 relates to an ultrasound diagnosis apparatus and discloses an arm mechanism on which a flat panel display is mounted as a display. At a connection section between a first arm and a second arm, a rotation mechanism is provided. The second arm comprises a parallel linkage so that the slanted angle of the second arm can be varied. Complex mechanisms are present inside the arm mechanism, in particular, in the second arm, and in the connection section. Therefore, it is difficult to thread a cable through the inside of the arm mechanism, and, when the cable passage is threaded, there is a possibility that the cable may be damaged, especially as it is threaded through the connection section.

In order to avoid unnecessarily blocking the movement of the display by the cable extending from the display and to not block the operation of the operation panel by the cable in an ultrasound diagnosis apparatus, it is desirable to route the cable through the inside of the arm mechanism. However, with such a configuration, if a bent structure with an acute angle is employed in the connection section similar to the related art, the cable tends to be damaged at the connection section, or the movement of the arm mechanism may be blocked. In consideration of exchange and maintenance of the display, it is desirable that the cable can be easily passed through and easily extended from the arm mechanism, and, thus, a threading structure which does not forcefully bend, but rather naturally curves, the cable is desired.

SUMMARY OF THE INVENTION

The present invention provides an advantageous ultrasound diagnosis apparatus including an arm mechanism through which a display cable of a display can be smoothly threaded, and in which the load on the cable when the position of the display is varied is reduced.

According to one aspect of the present invention, there is provided an ultrasound diagnosis apparatus comprising a base member, a display which is a flat panel display and which displays an ultrasound image, and an arm mechanism provided between the base member and the display and which varies a position of the display while holding the display, wherein the arm mechanism comprises a first arm member supported by the base member, a second arm member supported by the first arm member, and an intermediate turning mechanism provided at a connection section between the first arm member and the second arm member, a cable reaching the display from the base member passes through an inside of the first arm member and the second arm member, and a bent portion comprising an upper end portion of the first arm member and a lower end portion of the second arm member has a U shape in a state of an original shape when a turning angle of the intermediate turning mechanism is 0°.

With this configuration, a display is supported by an arm mechanism. The arm mechanism comprises a first arm member and a second arm member. The first arm member is supported on a base member, preferably in a turnable manner. The second arm member can turn with respect to the first arm member by an intermediate turning mechanism. With this structure, a horizontal position of the display can be varied. The second arm supports the display, desirably in a manner to allow turning.

A bent portion has a U shape in its initial state. That is, an upper end portion of the first arm and a lower end portion of the second arm are both formed as gently curved sections. When a cable is passed through the inside of these portions, the cable need not be excessively bent, and, thus, it is possible to naturally curve the cable. In particular, even when the intermediate turning mechanism transitioned from the state of the original shape and is in a rotated state, it is possible to prevent application of excessive forces beyond a natural torsion force to the cable. Alternatively, it is also possible to employ a configuration in which the upper end portion and the lower end portion have a symmetric shape with respect to a horizontal rotation surface. Because the display is formed as a flat panel display, it is not necessary for the arm mechanism to support a display as heavy as the CRTs of the related art. Constraints and conditional requirements for the arm mechanism are therefore relaxed, making it possible to increase the degree of freedom of the form of the arm mechanism. With the above-described arm mechanism, it is possible to realize appropriate positioning of a cable.

According to another aspect of the present invention, it is preferable that, in the ultrasound diagnosis apparatus, one of the upper end portion and the lower end portion has a J shape and the other one of the upper end portion and the lower end portion has an inverted J shape. The two mirror-image J shapes are then connected to form the U shape.

According to another aspect of the present invention, it is preferable that, in the ultrasound diagnosis apparatus, each of the upper end portion and the lower end portion has a circular horizontal cross section, and the intermediate turning mechanism is built in across both of the upper end portion and the lower end portion. According to another aspect of the present invention, it is preferable that, the ultrasound diagnosis apparatus further comprises a lock mechanism which locks an operation of the intermediate turning mechanism. Such a lock mechanism or a click mechanism which maintains each angle or a specific angle can be provided in each turning mechanism.

According to another aspect of the present invention, it is preferable that the ultrasound diagnosis apparatus further comprises a lower turning mechanism provided at a base end portion of the first arm member and connected to the base member, and an upper turning mechanism provided at a working end portion of the second arm member and which supports the display.

According to another aspect of the present invention, it is preferable that, in the ultrasound diagnosis apparatus, the first arm member comprises a slanted portion which extends from the base member toward a slanted upward direction and has a slanted axis, and a gently curved portion which connects between the slanted portion and the upper end portion and has an axis which transitions from a slanted state to a horizontal state. Because the slanted portion and the curved portion are connected, physical interference (collision) with structures present on an upper side of the apparatus body, such as an operation panel or the like, can be avoided (a lower space of the connection section having a U shape can be secured or increased) and the degree of change of the angle of axis at the curved portion can be alleviated (stress generated on the cable at that portion can be reduced). It is preferable that a portion having the largest bending angle of the cable in the passage route in the arm member is set as connection sections. Because the bending angle at this portion can be significantly alleviated as described above, no excessive load on the cable is generated. The degree of freedom of the cable can be increased when the bending angle is alleviated in portions before or after the connection section, and, thus, even when a torsion force is applied on the cable due to a turning movement at the connection section, this force can be distributed over a wide area of the cable.

According to another aspect of the present invention, it is preferable that, in the ultrasound diagnosis apparatus, the cable passes through the bent portion along an outer route which is displaced in the horizontal direction from a center axis of vertical rotation. With this structure, the bending angle of the cable can be increased and the load created on the cable can be reduced. In addition, because an axis member can be provided at a center of the turning mechanism, no waste space is created and a size of the turning mechanism itself can be reduced. When the U shape is to be designed, it is desirable to determine the U shape by calculating a limit radius of curvature of the cable and setting the actual radius of curvature to be greater than or equal to the limit radius of curvature at each position on the cable passage route.

DESCRIPTION OF PREFERRED EMBODIMENT

A preferred embodiment of the present invention will now be described with reference to the drawings.

Figure 1:
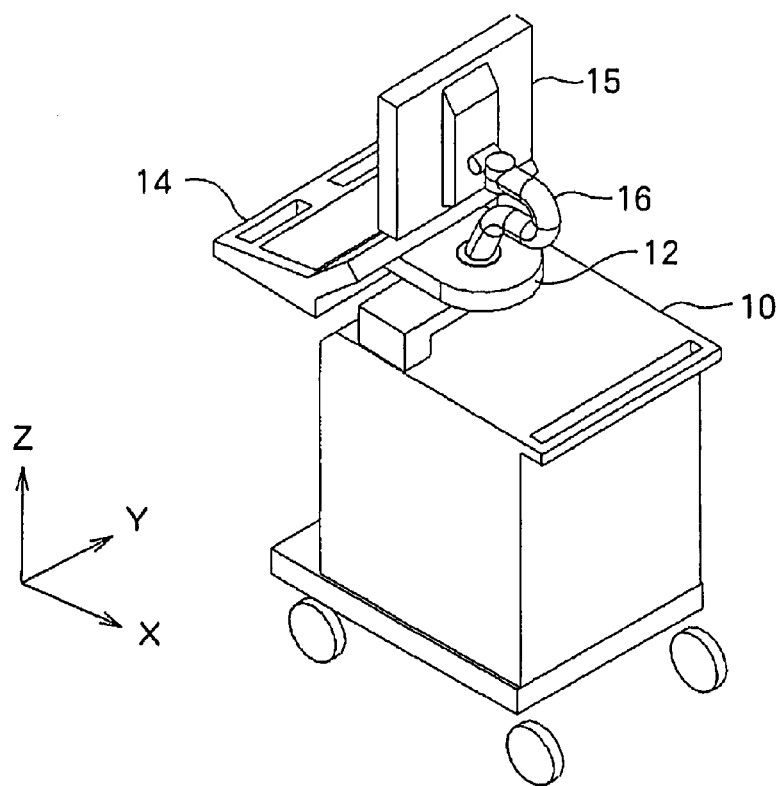
FIG. 1 is a schematic diagram schematically showing a structure of an ultrasound diagnosis apparatus according to a preferred embodiment of the present invention.

FIG. 1 is a schematic diagram of an ultrasound diagnosis apparatus according to a preferred embodiment of the present invention. The ultrasound diagnosis apparatus is a device which transmits and receives an ultrasound to and from a living body and forms an ultrasound image such as a tomographic image based on the reception signal thus obtained. In FIG. 1, an ultrasound probe which transmits and receives the ultrasound is not shown.

As shown in FIG. 1, the ultrasound diagnosis apparatus comprises a device body 10 which is a cart, a base member 12 supported by the device body 10, an operation panel 14 supported by the base member 12, an arm mechanism 16 supported by the base member 12, and a display 15 supported by the arm mechanism 16. A plurality of electronic circuit boards are built in the apparatus body 10. The base member 12 can be moved upward and downward directions by a support column. The operation panel 14 comprises a keyboard and a track ball, and a user can input and set various operations using the operation panel 14. The display 15 is constructed as a flat panel display in the present embodiment. An ultrasound image is displayed on the display 15. Alternatively, it is also possible to provide a CRT in place of the flat panel display. However, the flat panel display has an advantage over a CRT in that the flat panel display is lighter and can be easier to handle.

The arm mechanism 16 will now be described in detail. In FIG. 1, an X direction is a first horizontal direction and a depth direction, a Y direction is a second horizontal direction and a width direction perpendicular to the depth direction, and a Z direction is a vertical direction. As is described in more detail below, the arm mechanism 16 has a shape slanted away from the base member 12 and then curved.

Figure 2:
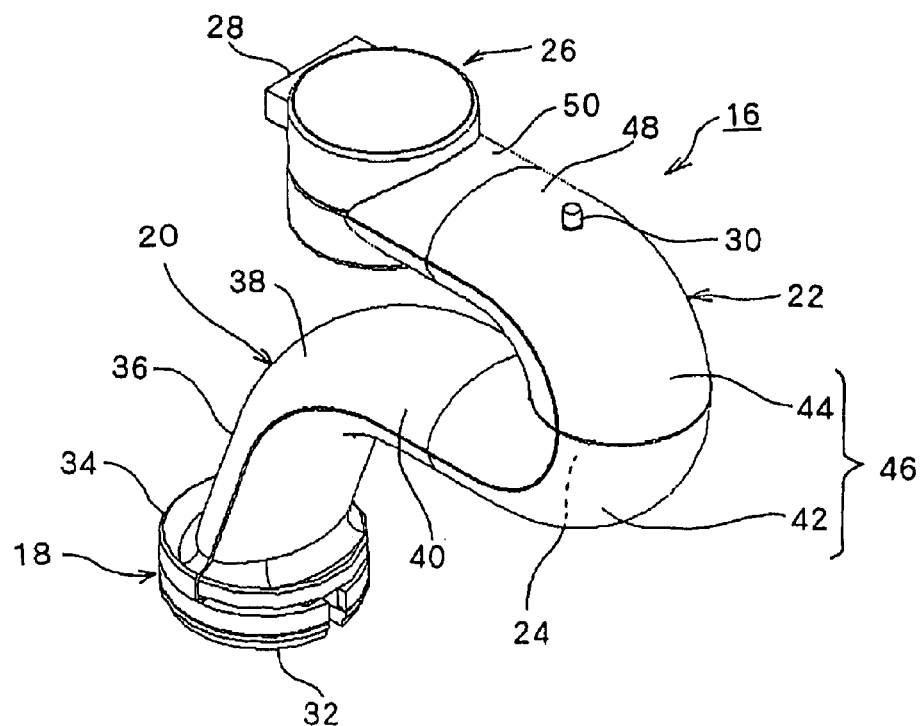
FIG. 2 is a schematic diagram showing an arm mechanism.

FIG. 2 is a schematic diagram of the arm mechanism 16. The arm mechanism 16 is supported by the base member shown in FIG. 1 and supports the display 15. The arm mechanism 16 comprises a plurality of joint portions for freely varying a position and an orientation of the display. The arm mechanism 16 comprises a first arm member 20 and a second arm member 22. In the arm members 20 and 22, an external side is a case and necessary components are stored inside the case.

A turning mechanism 18 is provided on a base end portion, which is a lower end portion of the first arm member 20. The turning mechanism 18 comprises a fixed ring-shaped member 32 and a rotational ring-shaped member 34, and these members rotationally move with respect to each other. The structure of these components will be described referring to FIG. 3.

Figure 3:
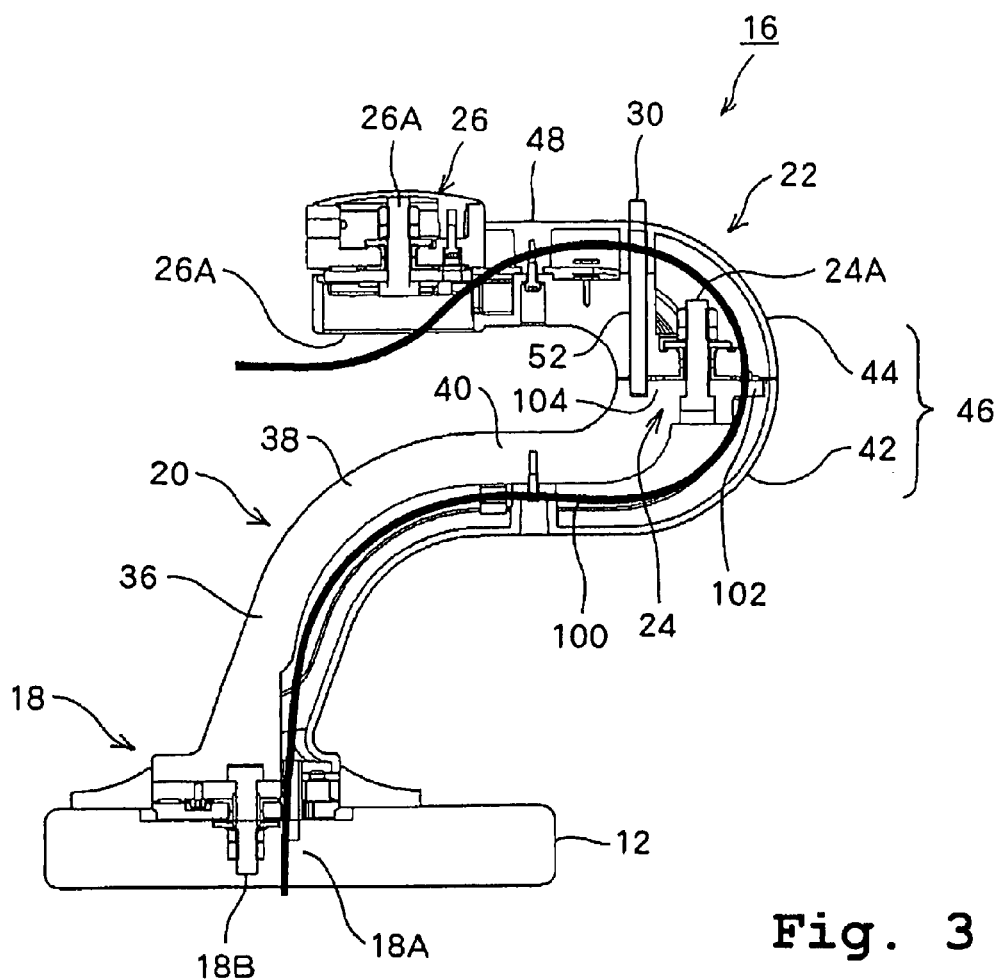
FIG. 3 is a cross sectional diagram showing an arm mechanism.

The first arm member 20 comprises a slanted portion 36 extending from the base end portion toward a slanted upward direction, a curved portion 38 connected to the slanted portion 36, and an upper end portion 42 which is connected to the curved portion 38 through a horizontal portion 40. As shown in FIG. 3, a horizontal cross-section of the slanted portion 36 is deformed and is an elliptical shape. The slanted portion 36 has a shape which is approximately straight, and the axis gradually transitions from the slanted state to a horizontal state by the curved portion 38. The angle of intersection between the axes of the slanted portion 36 and the horizontal portion 40 is an obtuse angle greater than 90° and smaller than 180°. The upper end portion 42 is connected to the horizontal portion 40, and the overall shape of the first arm member 20 is that of a horizontally inverted capital 'J'. An upper end of the upper end portion 42 reaches upwards in a vertical direction, with its uppermost surface in the shape of a full circle.

The second arm member 22 comprises a lower end portion 44 and a working end portion 50 connected to the lower end portion 44 through a horizontal portion 48. The lower end portion 44 is J-shaped (a horizontally inverted 'J'). The upper end portion 42 of the first arm member 20 and the lower end portion 44 of the second arm member 22 are combined to form a connection section 46. In its original state, in which the intermediate turning mechanism 24 (described later) is not turned (the rotation angle is 0°), the connection section 46 is U-shaped.

A turning mechanism 26 is connected to the working end portion 50 of the second arm member 22. The turning mechanism 26 comprises a mounting section 28 to which a display shown in FIG. 1 is connected. Alternatively, it is also possible to provide another joint member such as a tilt mechanism and a slide mechanism between the mounting section 28 and the display 15. At the turning mechanism 26, one of an upper half and a lower half is a fixed portion and the other one of the upper half and the lower half is a rotation portion. In the example configuration, the turning mechanism 26 is configured such that the upper half is turnable relative to the lower half.

In the connection section 46, that is, in a bent section across the upper end portion 42 and the lower end portion 44, an intermediate turning mechanism 24 is provided. Both the upper end portion 42 and the lower end portion 44 have a circular end surface, and the intermediate turning mechanism 24 has a function to turn the arm members 20 and 22 relative to each other in the horizontal direction while maintaining a joined state between their end surfaces. The connection section 46 has a U shape in the above-described state of original shape and both the upper end portion 42 and the lower end portion 44 have a gently curved shape. Therefore, as will be described later, even when a cable is passed through the connection section 46, it is possible to prevent application of excessive force on the cable. A lock mechanism is provided in the second arm member 22, and a knob 30 switches between an ON operation and an OFF operation of the lock mechanism. By operating the lock mechanism, it is possible to lock the turning position at the intermediate turning mechanism 24, and, in particular, in the present embodiment, it is possible to maintain the state of a turning angle of 0°. Such a lock mechanism may be provided on the turning mechanism 18 and turning mechanism 26, or it is also possible to employ, in each turning mechanism, a mechanism which gives a clicking feeling to a user at a predetermined angle interval.

FIG. 3 shows a vertical cross section of the arm mechanism shown in FIG. 2 seen from the direction of a side surface. The arm mechanism 16 shown in FIG. 3 is in the above-described state of original shape, with none of the turning mechanisms applying a turning operation, that is, all turning angles are 0°. As described, the first arm member 20 comprises a slanted portion which extends towards a slanted upward direction, a curved portion 38, and an upper end portion 42. The first arm member 20 curves towards a horizontal direction and bends towards the upward direction. However, the curvature at the curving and bending portion are gentle. In other words, there are no acute connections between members. Because of this structure, damage to a cable 100 can be minimized. This also applies to the second arm member 22. Because the lower end portion 44 of the second arm member 22 has a gently curved shape, the cable 100 can be protected.

Still referring to FIG. 3 for further explanation, the turning mechanism 18 comprises a rotation axis 18B which passes through the center of the turning mechanism 18 and which extends in a vertical direction. The cable 100 is passed through at the back of the rotation axis 18B, at a position shown by a reference numeral 18A. The turning mechanism 18 is thus configured such that no unnecessary load is applied to the cable 100 even with the turning by the turning mechanism 18. The cable 100 passes through the inside of the first arm member 20, that is, through the inside of the slanted portion 36 and the curved portion 38, and reaches the connection section 46.

The above-described intermediate turning mechanism 24 is built into the connection section 46. At the center of the connection section 46, an axis member 24A is provided along the vertical direction. The axis member 24A forms a center axis for turning. An inner side 104 and an outer side 102 seen from the center axis in the gentle bending shape can be defined. Of the inner side and the outer side, the cable 100 passes through the outer side 102. In other words, the cable 100 passes through the connection section 46 having a U shape along a side with a more gentle curve, that is, along the outer route. With this structure, it is possible to prevent application of an unnecessarily excessive force to the cable 100 even when the second arm member 22 is swiveled with respect to the first arm member 20. In addition, even when a torsion of the cable 100 is generated due to turning, because the bending radius of the cable 100 at the connection section 46 is very large, it is possible to prevent the problem of generation of local stress by absorbing the torsion force over a wide area. A lock pin 52 connected to the knob 30 forms a part of the lock mechanism. The operation of the intermediate turning mechanism 24 can be stopped by the operation of the lock pin 52, and, thus, the state of the original shape can be maintained.

The cable 100 also passes through the second arm 22. Here, too, the cable 100 is provided along the outer route, and extends to the side of the display through an opening 26A formed at a lower portion of the turning mechanism 26. In other words, as shown in FIG. 3, regarding the cable 100 connected to the display, there is no excessive local bending over the entire cable 100. In addition, because the radius of curvature in the bent portion or in the curved portion is large, the load on the cable can be reduced. Moreover, as will be described below, even when the turning mechanisms operate, the load on the cable 100 can be reduced.

Figure 4:
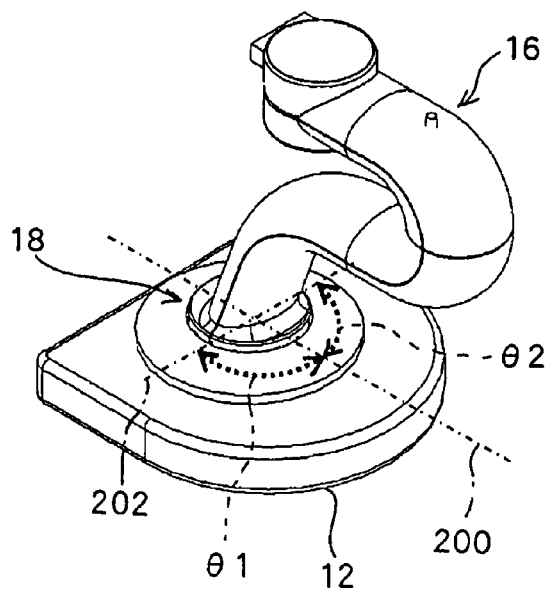
FIG. 4 is a diagram for explaining an operation of a lower turning mechanism.
Figure 5:
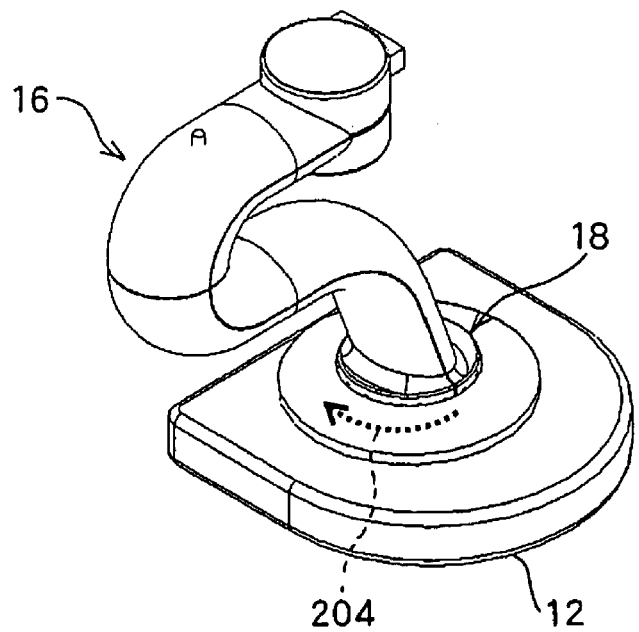
FIG. 5 is a diagram showing an operation state of a lower turning mechanism.
Figure 6:
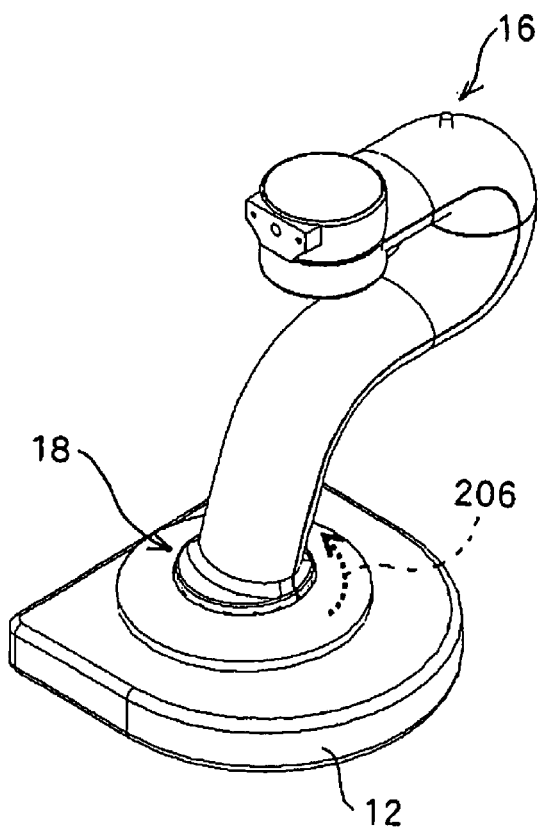
FIG. 6 is a diagram showing an operation state of a lower turning mechanism similar to FIG. 5.

FIG. 4 illustrates operation of the turning mechanism 18. Reference numeral 200 represents a reference axis which is parallel to the X direction of FIG. 1, and reference numeral 202 represents a reference axis which is parallel to the Y direction shown in FIG. 1. The axis shown with reference numeral of 200 corresponds to a rotation angle of 0°, and the arm mechanism 16 can be rotated to the left and right from that position. The turning range is shown with θ1 and θ2. Each of the angles θ1 and θ2 is 90°, and, thus, the turning mechanism 18 has a turning range of 180°. In other words, the turning range is limited to 180°. FIG. 5 shows a state in which the arm mechanism 16 is rotated in one direction, while FIG. 6 shows a state in which the arm mechanism 16 is rotated in the opposite direction (refer to reference numerals 204 and 206).

Figure 7:
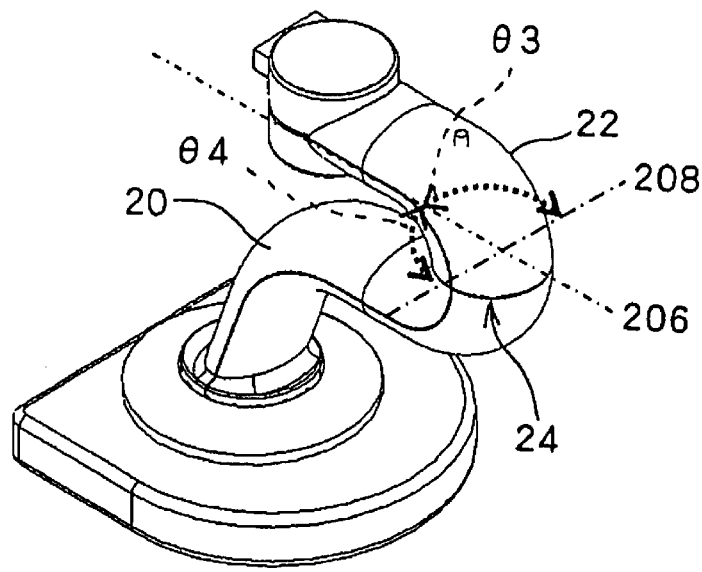
FIG. 7 is a diagram for explaining an operation of an intermediate turning mechanism.
Figure 8:
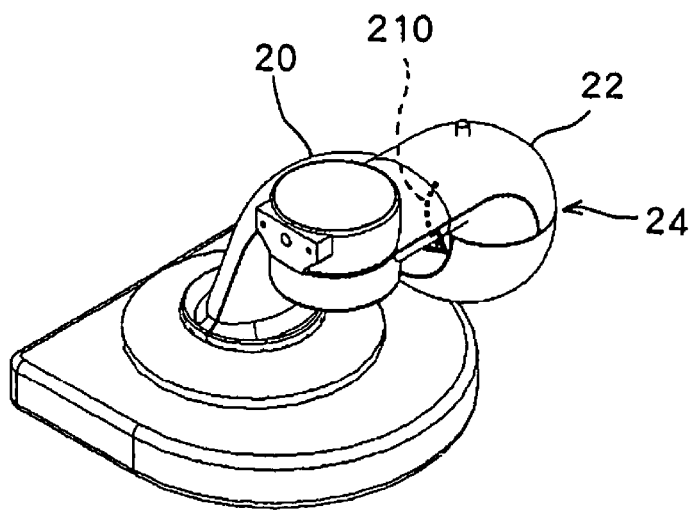
FIG. 8 is a diagram showing an operation state of an intermediate turning mechanism.
Figure 9:
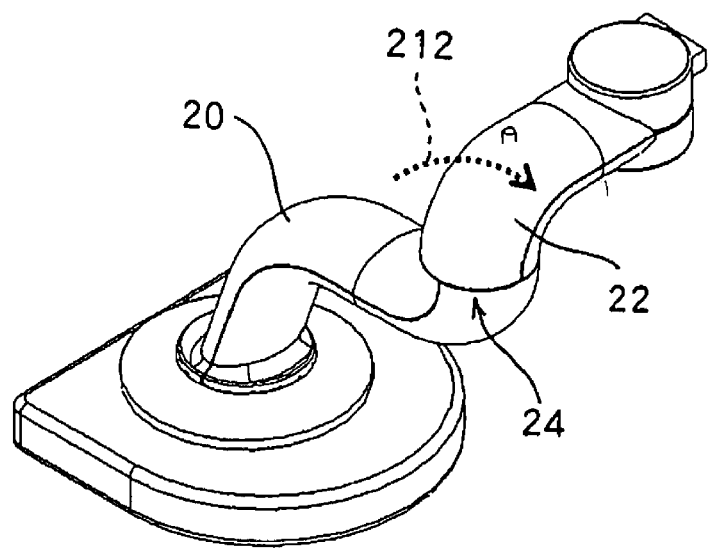
FIG. 9 is a diagram showing an operation state of an intermediate turning mechanism similar to FIG. 8.

FIG. 7 shows an operation of the intermediate turning mechanism 24. The axis 206 shows a reference axis when the first arm member 20 is used as a reference. Reference numeral 208 represents an axis perpendicular to the reference axis 206. Angles θ3 and θ4 represent a turning range, and, as shown in FIG. 7, the second arm member 22 turns and moves in a range of 180° with respect to the first arm member 20. In other words, the turning range is limited to 180°. FIG. 8 shows a state in which the second arm member 22 is rotated by 90° along a direction shown by reference numeral 210 relative to the first arm member 20 and FIG. 9 shows a state in which the arm member 22 is rotated by 90° along a direction shown by reference numeral 212 relative to the arm member 20. As shown in the figures, an intersecting relationship (intersecting relationship seen from the top) between the first arm member 20 and the second arm member 22 can be freely set with the intermediate turning mechanism 24, and, with this structure, the position of the display in the horizontal direction can be easily determined. In addition, there is also an advantage that, by operating both the lower turning mechanism and the upper turning mechanism, it is possible to more freely set the position and the orientation of the display.

Figure 10:
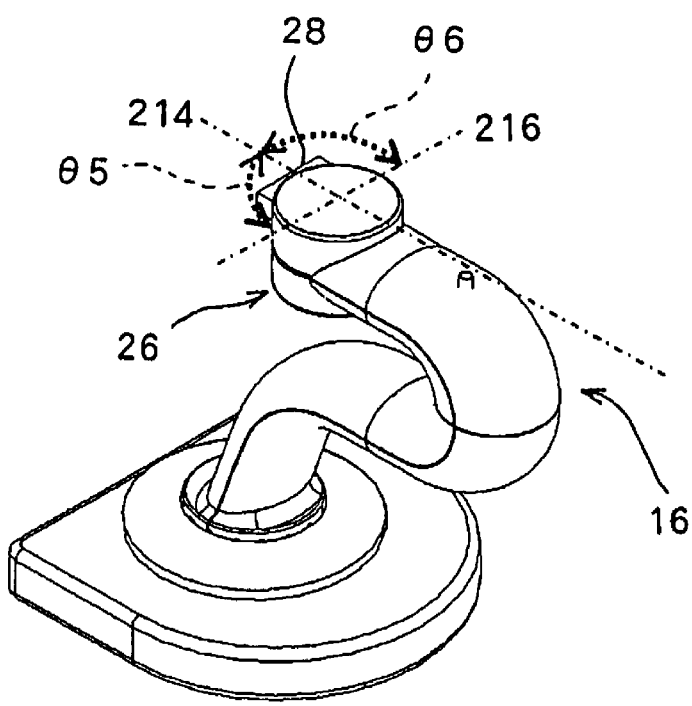
FIG. 10 is a diagram for explaining an operation of an upper turning mechanism.
Figure 11:
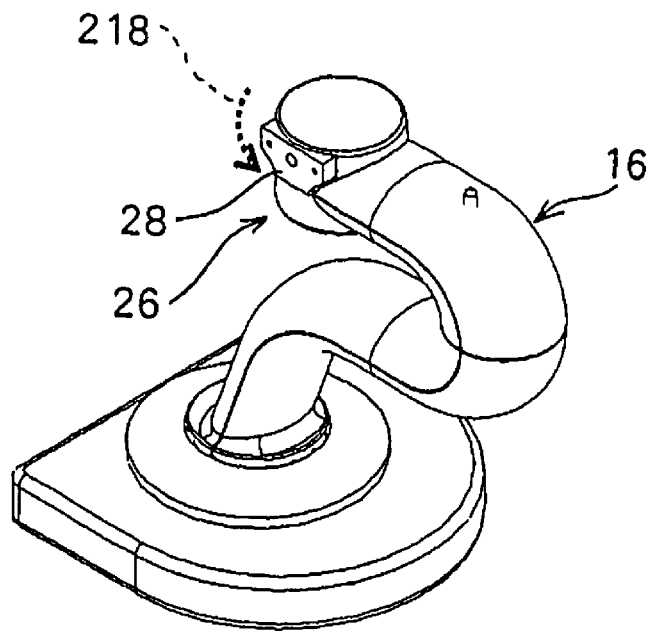
FIG. 11 is a diagram showing an operation state of an upper turning mechanism.
Figure 12:
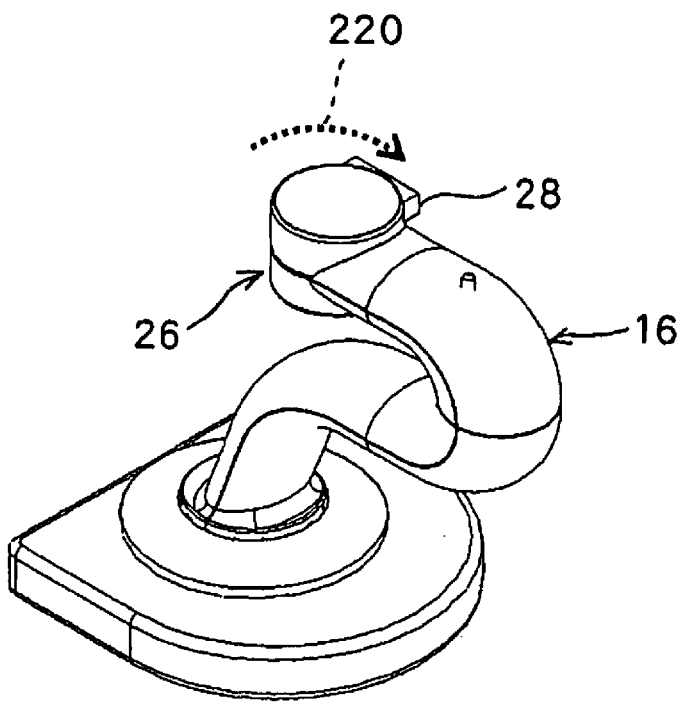
FIG. 12 is a diagram showing an operation state of an upper turning mechanism similar to FIG. 11.

FIG. 10 illustrates operation of the turning mechanism 26. Reference numeral 214 represents a reference axis with a reference on the second arm member 22 and reference numeral 216 represents a reference axis which is perpendicular to the reference axis. As shown in FIG. 10, the turning range is shown with angles θ5 and θ6, and is 180°. In other words, the turning angle is limited to 180°. Reference numeral 28 represents a mounting section of the display. FIG. 11 shows a state in which the mounting section 28 is turned by 90° along the direction shown by reference numeral 218 relative to the second arm member. FIG. 12 shows a state in which the mounting section 28 is turned by 90° along a direction shown by reference numeral 220 relative to the second arm member.

As described, according to the present embodiment, because three turning mechanisms each having a vertical rotational axis are provided in three stages including an upper stage, a middle stage, and a lower stage, the turning angles of the two arm members can be arbitrarily set so that the position of the display can be freely adjusted. In addition, there is also an advantage that the movable range can be widened. Still further, because the first arm member extends in a slanted upward direction and then in the horizontal direction, there is an advantage that a possibility of physical collision of the second arm member with the operation panel and other devices provided on an upper surface of the device can be reduced. Because the connection section has a U shape, the load on the cable passing inside of the connection section can be reduced. In particular, because the cable extends along an outer route inside the connection section, there is an advantage that the radius of curvature of the cable can be increased and the torsion force can be distributed over a wide range. Because the cable passes through the inside of the arm mechanism in such a mechanism, the various problems which occur when the cable extends outside of the arm mechanism can be prevented, and the appearance is not degraded. In addition, in the present embodiment each turning mechanism has an axis member at the center position. Because of this structure, turning can be realized by a simple structure using the axis member as the rotation axis, and, thus, the size of each turning mechanism can be reduced.

Although the preferred embodiments of the present invention have been described using specific terms, such description is for illustrative purposes only, and it is to be understood that modifications and variations may be made without departing from the spirit or scope of the appended claims.

What is claimed is:

1. An ultrasound diagnosis apparatus comprising:
a base member;
a display which is a flat panel display and which displays an ultrasound image; and
an arm mechanism provided on an upper side of the base member and between the base member and the display and which varies a position of the display while holding the display,
wherein the arm mechanism comprises:
a first arm member supported by the base member,
a second arm member supported by the first arm member, and
an intermediate turning mechanism provided at a connection section between the first arm member and the second arm member;
a cable reaching the display from the base member passes through an inside of the first arm member and the second arm member; and
a bent portion comprising an upper end portion of the first arm member and a lower end portion of the second arm member has a U shape in a state of an original position when a turning angle of the intermediate turning mechanism is 0°,
wherein the upper end portion of the first arm member and the lower end portion of the second arm member respectively have a gently curved shape, and
wherein the upper end portion of the first arm member and the lower end portion of the second arm member are connected via a horizontal rotation surface in a manner that the first arm member is not vertically movable with respect to the second arm member, and the second arm member is not vertically moveable with respect to the first arm member, and the upper end portion of the first arm member and the lower end portion of the second arm member have a mirror image symmetric shape with respect to the horizontal rotation surface in the state of the original position, and
wherein the first arm member comprises:
a slanted portion which extends from the base member toward a slanted upward direction and has a slanted axis; and
a gently curved portion which connects between the slanted portion and the upper end portion and has an axis which transitions from a slanted state to a horizontal state.

2. The ultrasound diagnosis apparatus according to claim 1, wherein
one of the upper end portion and the lower end portion has a J shape and the other one of the upper end portion and the lower end portion has a horizontally inverted J shape.

3. The ultrasound diagnosis apparatus according to claim 2, wherein
each of the upper end portion and the lower end portion has a circular horizontal cross section; and
the intermediate turning mechanism is built in across both of the upper end portion and the lower end portion.

4. The ultrasound diagnosis apparatus according to claim 1, further comprising:
a lock mechanism which locks an operation of the intermediate turning mechanism.

5. The ultrasound diagnosis apparatus according to claim 1, further comprising:
a lower turning mechanism provided at a base end portion of the first arm member and connected to the base member; and an upper turning mechanism provided at a working end portion of the second arm member and which supports the display.

6. An ultrasound diagnosis apparatus, comprising:

a base member;

a display which is a flat panel display and which displays an ultrasound image; and an arm mechanism provided between the base member and the display and which varies a position of the display while holding the display, wherein the arm mechanism comprises:

a first arm member supported by the base member, a second arm member supported by the first arm member, and an intermediate turning mechanism provided at a connection section between the first arm member and the second arm member;

a cable reaching the display from the base member passes through an inside of the first arm member and the second arm member; and a bent portion comprising an upper end portion of the first arm member and a lower end portion of the second arm member has a U shape in a state of an original position when a turning angle of the intermediate turning mechanism is 0°, wherein the upper end portion of the first arm member and the lower end portion of the second arm member are connected via a horizontal rotation surface in a manner that the first arm member is not vertically moveable with respect to the second arm member, and the second arm member is not vertically moveable with respect to the first arm member, and the upper end portion of the first arm member and the lower end portion of the second arm member have a mirror image symmetric shape with respect to the horizontal rotation surface in the state of the original position, and wherein the first arm member comprises:

a slanted portion which extends from the base member toward a slanted upward direction and has a slanted axis; and a gently curved portion which connects between the slanted portion and the upper end portion and has an axis which transitions from a slanted state to a horizontal state.

7. The ultrasound diagnosis apparatus according to claim 1, wherein the cable passes through the bent portion along an outer route which is displaced in the horizontal direction from a center axis of vertical rotation within the bent portion.

\* \* \* \* \*